United States Patent [19]

Curry

[11] Patent Number: 4,497,326
[45] Date of Patent: Feb. 5, 1985

[54] HEART PACING LEAD

[76] Inventor: Paul V. L. Curry, 6 Windermere Rd., Kingston Vale, London SW15 3QP, England

[21] Appl. No.: 365,707

[22] Filed: Apr. 5, 1982

[30] Foreign Application Priority Data

Apr. 6, 1981 [GB] United Kingdom ............... 8110732
Jan. 29, 1982 [GB] United Kingdom ............... 8202539

[51] Int. Cl.³ ............................................. A61N 1/04
[52] U.S. Cl. ................................... 128/785; 128/786
[58] Field of Search ........................ 128/784-786, 128/419 P

[56] References Cited

U.S. PATENT DOCUMENTS

| | | | |
|---|---|---|---|
| 3,949,757 | 4/1976 | Sabel | 128/419 P |
| 3,977,411 | 8/1976 | Hughes | 128/419 P |
| 4,057,067 | 11/1977 | Lajos | 128/419 P |
| 4,142,530 | 3/1979 | Wittkampf | 128/419 P |
| 4,146,036 | 3/1979 | Dutcher | 128/419 P |
| 4,154,247 | 5/1979 | O'Neill | 128/419 P |
| 4,233,992 | 11/1980 | Bisping | 128/785 |
| 4,289,144 | 9/1981 | Gilman | 128/785 |
| 4,332,259 | 6/1982 | McCorkle, Jr. | 128/786 |
| 4,386,615 | 6/1983 | Sowton | 128/786 |
| 4,393,883 | 7/1983 | Smyth et al. | 128/785 |
| 4,402,329 | 9/1983 | Williams | 128/785 |

FOREIGN PATENT DOCUMENTS

| | | |
|---|---|---|
| 2605590 | 8/1977 | Fed. Rep. of Germany |
| 2822829 | 11/1979 | Fed. Rep. of Germany |
| 1119615 | 7/1968 | United Kingdom |
| 1537101 | 12/1978 | United Kingdom |

*Primary Examiner*—Lee S. Cohen
*Attorney, Agent, or Firm*—Salter & Michaelson

[57] ABSTRACT

A transvenous heart pacing lead has atrial and ventricular electrodes enabling both atrial and ventricular pacing or sequential pacing. The atrial electrode is mounted either directly on the main lead body or on an atrial lead portion branching from the lead body. A barbed or other fixing element is mounted in the atrial electrode and can be forced outward by means of a guide wire so as to anchor the electrode to the atrial wall. In this way it is ensured that good electrical contact is maintained permanently.

6 Claims, 7 Drawing Figures

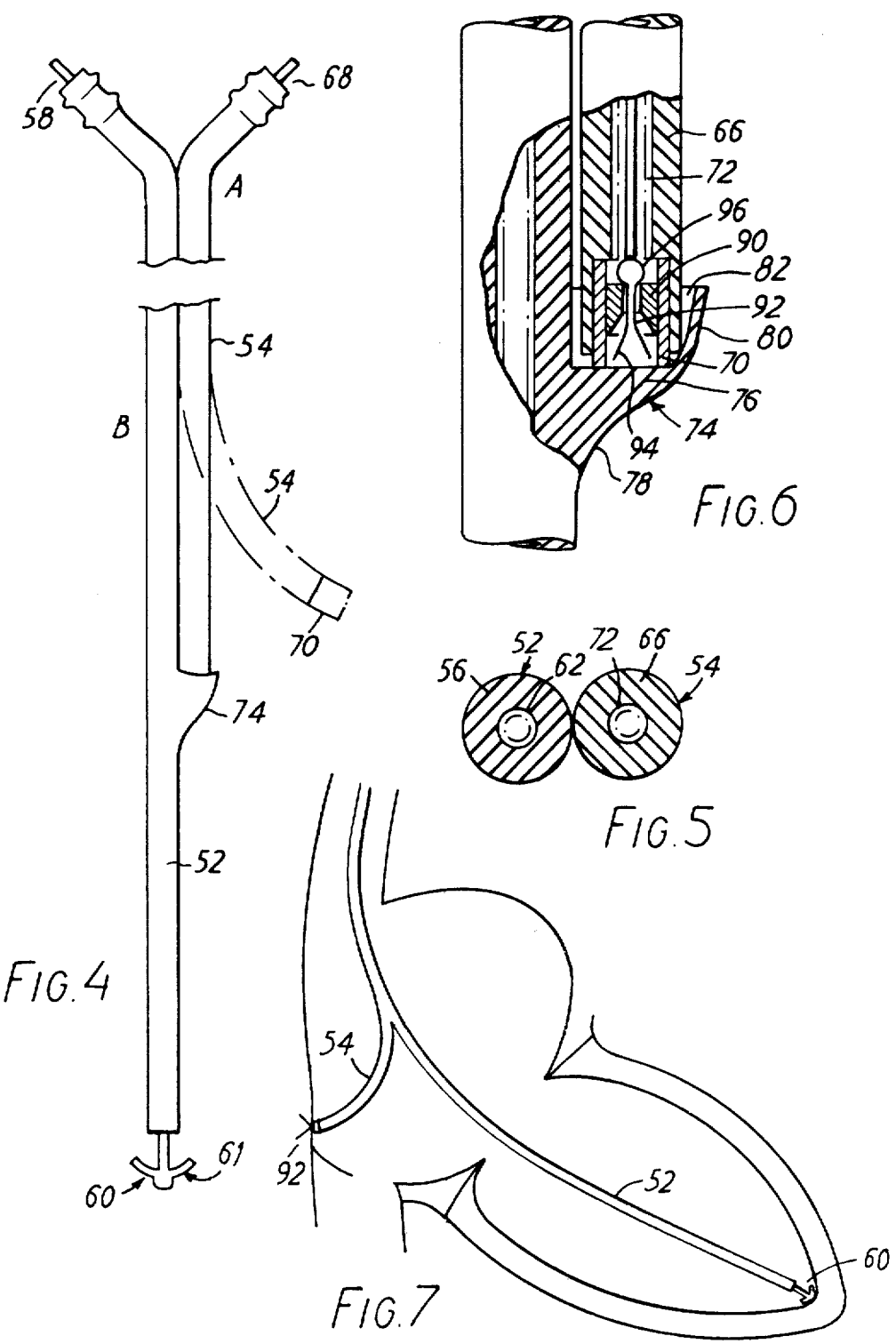

HEART PACING LEAD

BACKGROUND OF THE INVENTION

1. Field of the invention

This invention relates to heart pacing and more particularly to transvenous heart pacing leads.

For certain patients, reasonable success can be achieved with a heart pacing system which paces the ventricle at an externally imposed rate. In some patients, where the atrium is functioning adequately but is not capable of triggering the ventricle, an improvement in heart performance could be achieved if electrical activity in the atrium were sensed and the ventricle paced in synchronism with natural movement of the atrium. Pacing would then be provided at the correct physiological rate rather than at an externally imposed rate. In other patients, where the atrium is not functioning adequately, an improvement over straightforward ventricular pacing could still be achieved if the atrium and ventricle were paced sequentially so that advantage were taken of the pumping capability of the atrium.

The major practical disadvantage of atrio-synchronous pacing of the ventricle and atrioventricular-sequential pacing has been the requirement for separate atrio and ventricular leads. For this reason the techniques have not been widely employed.

2. Description of the prior art

It has been suggested, (The Lancet-Oct. 7th, 1978 pages 757 to 759) that an atrial electrode could be mounted on an otherwise conventional lead in the form of a small sleeve positioned approximately 13 to 18 cm from the ventricular electrode. With this arrangement, the sleeve electrode lies within the atrium when the ventricular electrode is in position and can be used to sense electrical activity in the atrium. There is—at best—intermittent contact with the atrial wall and although this arrangement is reasonably satisfactory for atrial sensing, the electrical contact with the atrium is insufficient to permit atrioventricular-sequential pacing.

It has further been suggested, (The Journal of Thoracic and Cardiovascular Surgery Volume 69 Number 4 April 1965 pages 575 to 578) that the atrial electrode could be mounted at the end of an atrial lead portion which branches from the main lead body. The atrial electrode is secured to the lead body during insertion of the lead and is released once the lead is in place by withdrawal of a guide wire to allow the atrial lead portion to take up its natural J-shape. This J-shape is intended to bring the atrial electrode into contact with the atrial wall and also serves to hinder retraction of the lead.

This lead has not become popular, probably because of difficulties in insertion and positioning. Even if the lead were correctly positioned with the atrial electrode in contact with the atrial wall, there is a risk of the electrical contact being impaired through subsequent movement of the atrial electrode. It will be appreciated that there is no natural "site" for location of the atrial electrode as there is with a ventricular electrode.

SUMMARY OF THE INVENTION

It is an object of this invention to provide an improved transvenous heart pacing lead which can be inserted in the same manner as a single lead but which enables ventricular and atrial electrodes to be positioned and maintained in good electrical contact with the walls of the ventricle and atrium respectively.

Accordingly, the present invention consists in a transvenous heart pacing lead comprising an elongate lead body; a ventricular electrode mounted at one end of the lead body; terminal means provided at the other end of the body for connection with a pacing device; first conductor means in the lead body establishing electrical contact between said ventricular electrodwe and said terminal means; an atrial electrode supported directly on the lead body such that the atrial electrode can in use be brought into contact with the atrial wall through manipulation of the lead body; second conductor means in the lead body establishing electrical contact between said atrial electrode and said terminal means; a bore extending longitudinally of the lead body enabling the introduction from said other end of the lead body of a guide wire; and a fixing element mounted in the atrial electrode for movement relative thereto, said fixing element being displaceable relative to the atrial electrode by means of the guide wire to anchor the atrial electrode to the atrial wall.

Advantageously, the atrial electrode is supported directly on the lead body such that the atrial electrode is in use brought into contact with the atrial wall through manipulation of the lead body after location of the ventricular electrode.

Suitably, the fixing means are operable by means of a guide wire extending longitudinally through the lead body.

In one form of this invention, the atrial electrode is supported at the end of a spur extending from the body, the atrial electrode being releasably secured to the body to facilitate insertion of the lead.

BRIEF DESCRIPTION OF THE DRAWINGS

The invention will now be described by way of example with reference to the accompanying drawings in which:

FIG. 4 is a view of a further heart pacing lead according to this invention, FIG. 5 is a cross-sectional view through the lead shown in FIG. 4

FIG. 6 is a view on an enlarged scale and partly in cross section of a region of the lead shown in FIG. 4, and FIG. 7 is a diagrammatic view showing the lead of FIG. 4 in position in the heart.

Figure 1:
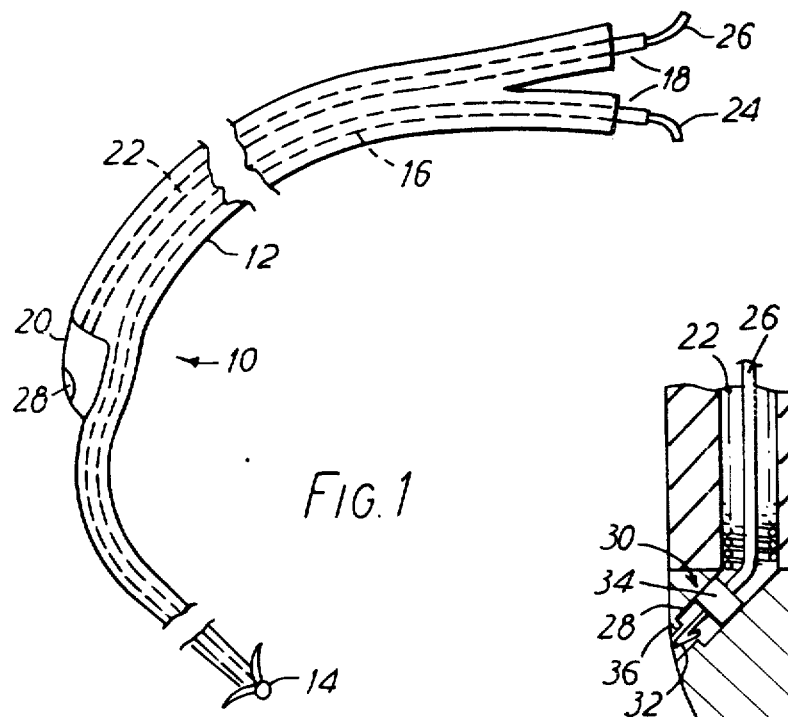
FIG. 1 is a view of a heart pacing lead according to this invention.
Figure 2:
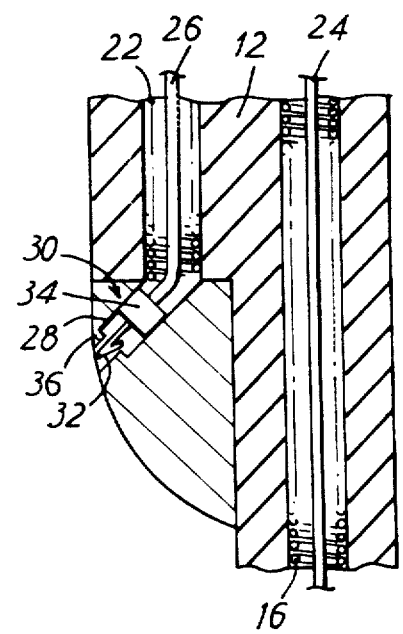
FIG. 2 is a view on an enlarged scale and partly in cross section of a region of the lead shown in FIG. 1.
Figure 3:
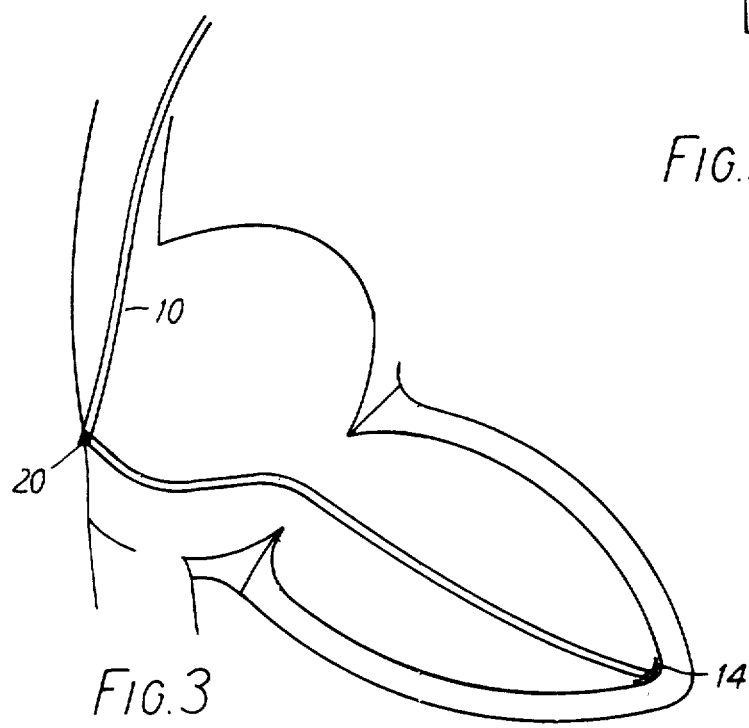
FIG. 3 is a diagrammatic view showing the lead according of FIG. 1 in position in the heart.

The heart pacing lead shown generally at 10 in FIGS. 1, 2 and 3 comprises a body 12 with a ventricular electrode 14 of generally conventional form at one end. The body 12 is formed of silicone rubber and the electrode 14 of a platinum-irridium alloy. A hollow conductor 16 in the form of a tightly wound helical coil extends the length of the lead to establish electrical contact between the ventricular electrode 14 and one of a pair of terminals 18 at the opposite end of the lead. The terminals 18 enable connection of the lead with a pacing device. At a suitable spacing from the ventricular electrode 14, which may be approximately 14 to 18 cm, the lead body 12 carries an atrial electrode 20 which is shaped to extend partially around the lead body. A second, hollow conductor 22 establishes electrical contact between this atrial electrode and the other one of the terminals 18. The atrial electrode 20 presents a streamlined appearance, the body being thicker immediately behind the atrial electrode to accommodate both conducting wires.

The hollow nature of the conductors 16 and 22 enables guide wires 24 and 26 to be inserted into the lead and for the purposes of installation.

The atrial electrode 20, as best seen in FIG. 2, is formed with a bore 28 which is open at one end and communicates at the other with the cylindrical cavity of the hollow conductor 22. The bore 28 is inclined at an angle of approximately 45 degrees to the length of the lead body. Within the bore 28 there is located a fixing element 30 having a barb 32 extending from a cylindrical portion 34 which is arranged to be a sliding fit within the bore. The fixing element 30 is retained within the atrial electrode by means of an inwardly directed flange 36 formed at the opening of the bore 28.

The manner in which the lead is installed can now be described with particular reference to FIG. 3 which includes a diagrammatical representation of the heart. The ventricular electrode is positioned at the apex of the right ventricle in a manner similar to that employed with single electrode leads. This done, the lead body is manipulated by means of the guide wires to bring the atrial electrode into contact with the atrial wall. Once a position has been found which gives good electrical contact, the fixing element 30 is driven into the atrial wall through axial movement of the guide wire 26. The two guide wires can then be withdrawn leving both the ventricular and atrial electrodes securely fastened in place.

It will be appreciated that the described method enables the ventricular electrode to be positioned and then—with the ventricular electrode substantially immobilized in the apex of the right ventricle—the atrial electrode can be maneuvered into an optimum position. By means of the fixing element, this optimum position of the atrial electrode is then permanently maintained.

The ventricular electrode 14 is preferably shaped in such a manner as to inhibit retraction from the apex of the ventricle. If thought necessary, the ventricular electrode can be provided with a "positive" fixing element which is operable from the terminal end of the lead, such as the described atrial fixing element. The need for a positive fixing element on the ventricular electrode is not so great, however, because whilst the atrial electrode must be secured to a generally flat wall, the ventricular electrode can be forced into the apex of the ventricle. The need for positive fixing of the ventricular electrode is less with the leads according to this invention than with conventional electrodes since anchoring of the lead at the postion of the atrial electrode plays a significant part in inhibiting movement of the ventricular electrode.

Referring now to the second embodiment of this invention illustrated in FIGS. 4, 5, 6 and 7, the lead comprises a ventricle lead portion 52 and an atrium lead portion 54 both of circular cross section. The ventricle lead portion comprises a body 56 of silicone rubber having at one end a terminal 58 and at the other a ventricular electrode 60. The electrode is formed with fins 61 to hold the electrode in place once positioned in the apex of the ventricle. Along the length of the lead portion there extends a hollow conductor 62 which establishes electrical contact between the electrode 60 and the terminal 58. The atrium lead portion 54 is shorter than the ventricle portion but similarly comprises a silicone rubber body 66, a terminal 68, an atrial electrode 70 and a hollow conductor 72.

The two lead portions are permanently bonded together from a point A adjacent the terminals to a point B approximately 5 cm from the atrial electrode. The free part of the atrial lead portion adjacent the electrode is normally held in contact with the ventricular portion as shown in full lines in FIG. 4, by means of the engagement of the atrial electrode with a housing, as will now be described.

Adjacent the atrial electrode 70, the body 56 of the ventricle lead portion is shaped to provide an integral housing 74, which comprises a base 76 presenting a streamlined profile 78 and a relatively thin wall 80 defining a cavity 82. The atrial electrode 70 is positioned with this cavity. The free or separable end part of the atrium lead portion is so formed that its natural shape is as shown in dotted outline in FIG. 4, that is to say curved away from the ventricle lead portion. This can be achieved for example by moulding the silicone rubber body in a suitably curved mould.

The atrial electrode 70 is formed with an internal bore in which there is slidably mounted a small chuck 90. This chuck carries a fixing element 92 which is of generally "hairpin" shape having two limbs 94 connected by a bight portion 96. In the retracted position, the two limbs 94 are housed within the bore of the electrode but from manipulation of the guide wire the fixing element can be slidably displaced to a position where the limbs project from the electrode. It will be seen that the ends of the limbs 94 are angled outwardly; this inclination increases as the fixing element is extended so that a reliable fixing to the atrial wall is achieved.

The lead is inserted into the venous system in the same manner as a unipolar lead with the streamlined profile 78 of the housing 74 facilitating insertion. Once the electrodes have entered the heart, the atrial electrode can be retracted from the housing through the combination of a "pushing" action on a guide wire inserted in the ventricle lead portion and a "pulling" action on the body of the atrium lead portion. By this means, the bond between the lead portions is elastically deformed in the longitudinal direction with sufficient longitudinal displacement being achieved at the housing 74 for the atrial electrode to be pulled free of the wall 80. In reverting to its natural shape, the atrial lead portion will then move away from the ventricle portion allowing the longitudinal stress in the lead portions to be released.

The freed atrial electrode is manoeuvred with the guide wire into a position of optimum electrical contact with the atrial wall. The guide wire is then pushed inwardly of the lead to drive the two limbs of the fixing element 92 into engagement with the atrial wall, thereby anchoring the atrial electrode in the position of optimum electrical contact.

A particularly good electrode for use as the atrial electrode in this embodiment is that made by BIO-TRONIK GmbH under their reference number I2.

It will be appreciated that this invention provides a heart pacing lead which enables good and reliable electrical contact to be made to both ventricle and atrium without unduly complicating the insertion or positioning procedures. The ability positively to anchor the atrial electrode offers the very important advantage of long term stability but also has the advantage important in both the short and long term that the atrial electrode can be anchored in a position giving optimum electrical contact even if that position is not one which the atrial portion of the lead would normally adopt.

This invention has been described by way of examples only and a variety of modifications are possible without departing from the scope of the appended claims. In particular, fixing means other than those described can be employed to anchor the atrial electrode to the atrial wall. For example, a "corkscrew" fixing element could be used which is screwed into the atrial wall through rotation of the atrial guide wire. The design of other suitable fixing elements operable from the remote end of the lead will be apparent to the skilled man. The ventricular electrode could take a wide variety of alternative forms, being produced—for example—from wire mesh or porous carbon, to promote tissue ingrowth.

The described arrangements employ an external plate of the implanted pacing device as the common ground electrode for both the atrial and ventricular electrodes. If necessary, a common ground electrode could be formed on the lead itself, spaced from the atrial and ventricular electrodes so as to lie in the superior vena cava.

The formation, in the second illustrated embodiment, of a lead by the bonding together of two lead portions facilitates the retraction—as described—of the atrial electrode from its housing and also admits of straightforward production techniques. It is possible, nonetheless, to produce the lead with an integral body which is forked toward the electrode end to provide separable atrial and ventricular lead portions. Techniques other than that described could be employed for retracting the atrial electrode from its housing; the atrial guide wire could for instance be shaped to engage the electrode as the guide wire is pulled backwards. Indeed, means other than an atrial electrode housing could be used to hold the lead portions together. The fixing element of the atrial electrode could be engaged into a ledge formed integrally with the ventricular lead portion; at the same position as the described housing. This technique could in fact be used in addition to; a housing, with the atrial fixing element being driven into the base of the housing. A further alternative is a coupling having complementary parts on the respective lead portions, separble by relative longitudinal displacement.

What is claimed is:

1. A transvenous heart pacing lead comprising an elongated lead body; a ventricular electrode mounted at one end of the lead body; terminal means provided at the other end of the body for connection with a pacing device; first conductor means in the lead body establishing electrical contact between said ventricular electrode and said terminal means; an atrial electrode supported directly on the lead body at a spaced location toward the said other end of the lead body such that the atrial electrode can in use be brought into contact with the atrial wall through manipulation of the lead body; second conductor means in the lead body establishing electrical contact between said atrial electrode and said terminal means; a bore extending longitudinally of the lead body enabling the introduction from said other end of the lead body of a guide wire; and a fixing element movably mounted in the atrial electrode between a first position within the electrode and a second position extending therefrom in response to manipulation of the guide wire to anchor the atrial electrode to the atrial wall.

2. A heart pacing lead according to claim 1, wherein said fixing element is located within a bore in the atrial electrode, said bore being inclined to the longitudinal direction of the lead body.

3. A heart pacing lead according to claim 2, wherein said bore is inclined at an angle of approximately 45° to the longitudinal direction of the lead body.

4. A transvenous heart pacing lead comprising:
   (a) an elongated lead body having a terminal end and an electrode end;
   (b) a ventricular electrode secured to the lead body at said electrode end thereof;
   (c) terminal means provided on the lead body at said terminal end thereof to enable electrical connection to be made to a pacing device;
   (d) a first hollow electrical conductor extending longitudinally within the lead body and establishing the electrical contact between said ventricular electrode and said terminal means, the hollow nature of the conductor enabling the introduction therealong of a first guide wire;
   (e) an atrial electrode secured to the lead body at a spaced location toward the terminal end of the lead body from said ventricular electrode;
   (f) a second hollow electrical conductor extending longitudinally within the lead body and establishing electrical contact between said atrial electrode and said terminal means, the hollow nature of the conductor enabling the introduction therealong of a second guide wire; and
   (g) a fixing element movably mounted in the atrial electrode between a first position within the electrode and a second position extending therefrom in response to manipulation of said second guide wire to anchor the atrial electrode to the atrial wall.

5. A transvenous heart pacing lead according to claim 4, wherein said fixing element is located within a bore in the atrial electrode, said bore being inclined to the longitudinal direction of the lead body.

6. A transvenous heart pacing lead according to claim 5, wherein said bore is inclined at an angle of approximately 45 degrees to the longitudinal direction of the lead body.

* * * * *